United States Patent
Yang et al.

(10) Patent No.: US 10,835,390 B2
(45) Date of Patent: Nov. 17, 2020

(54) METHOD FOR MANUFACTURING BONE GRAFT MATERIAL AND BONE GRAFT MATERIAL MANUFACTURED THEREBY

(71) Applicants: ELECTRONICS AND TELECOMMUNICATIONS RESEARCH INSTITUTE, Daejeon (KR); Korea Textile Machinery Convergence Research Institute, Gyeongsan (KR)

(72) Inventors: So Young Yang, Daegu (KR); Yong Il Chung, Daegu (KR); Kyu Hyung Kim, Daegu (KR); Min Ji Lee, Gyeongsan (KR); Soo In Lee, Daejeon (KR); Eun Chang Choi, Daegu (KR)

(73) Assignees: ELECTRONICS AND TELECOMMUNICATIONS RESEARCH INSTITUTE, Daejeon (KR); Korea Textile Machinery Convergence Research Institute, Gyeongsan (KR)

( * ) Notice: Subject to any disclaimer, the term of this patent is extended or adjusted under 35 U.S.C. 154(b) by 94 days.

(21) Appl. No.: 16/216,484

(22) Filed: Dec. 11, 2018

(65) Prior Publication Data
US 2019/0216616 A1    Jul. 18, 2019

(30) Foreign Application Priority Data
Jan. 15, 2018    (KR) .................. 10-2018-0004840

(51) Int. Cl.
*A61F 2/28* (2006.01)
*A61F 2/46* (2006.01)
(Continued)

(52) U.S. Cl.
CPC ........ *A61F 2/4644* (2013.01); *A61C 13/0019* (2013.01); *A61F 2/28* (2013.01);
(Continued)

(58) Field of Classification Search
CPC ........................................................ A61F 2/28
See application file for complete search history.

(56) References Cited

U.S. PATENT DOCUMENTS

| | | | |
|---|---|---|---|
| 6,605,293 B1 * | 8/2003 | Giordano | ............... A61L 27/42 |
| | | | 424/423 |
| 2017/0027671 A1 | 2/2017 | Kim et al. | |

FOREIGN PATENT DOCUMENTS

KR    101357673 B1    2/2014

OTHER PUBLICATIONS

Lin et al (Acta Biomaterialia, vol. 10, Issue 10, Oct. 2014, pp. 4071-4102). (Year: 2014).*

(Continued)

*Primary Examiner* — Benjamin J Packard

(57) ABSTRACT

The present invention relates to a method for manufacturing a bone graft material using 3D printing of a DLP system. The method includes (1) dispersing a powder material including calcium phosphate-based ceramics in a solvent; (2) recovering the calcium phosphate-based ceramics by removing the solvent from a solution in which the calcium phosphate-based ceramic material is dispersed in Step 1; (3) producing a photocurable resin composition by adding a binder resin including a crosslinking agent and a photoinitiator to the calcium phosphate-based ceramics obtained in Step 2; (4) performing 3D rapid prototyping on a bone graft material molded body from the composition for a bone graft material produced in Step 3 by 3D printing of a DLP system; and (5)

(Continued)

debinding and sintering organic materials remaining in the bone graft material molded body subjected to prototyping in Step 4.

19 Claims, 7 Drawing Sheets

(51) Int. Cl.
    *A61C 13/00*     (2006.01)
    *A61L 27/12*     (2006.01)
    *A61L 27/56*     (2006.01)
    *B33Y 80/00*     (2015.01)
    *A61L 27/50*     (2006.01)
    *B33Y 70/00*     (2020.01)
    *A61L 27/32*     (2006.01)
    *B33Y 10/00*     (2015.01)
    *A61L 27/36*     (2006.01)

(52) U.S. Cl.
    CPC ............ *A61F 2/4601* (2013.01); *A61L 27/12* (2013.01); *A61L 27/50* (2013.01); *A61L 27/56* (2013.01); *B33Y 80/00* (2014.12); *A61F 2310/00293* (2013.01); *A61F 2310/00359* (2013.01); *A61F 2310/00796* (2013.01); *A61L 27/32* (2013.01); *A61L 27/3608* (2013.01); *A61L 2430/02* (2013.01); *B33Y 10/00* (2014.12); *B33Y 70/00* (2014.12)

(56) References Cited

OTHER PUBLICATIONS

Nie (European Polymer Journal, vol. 35, Issue 8, Aug. 1999, pp. 1491-1500). (Year: 1999).*

Stansbury et al (Dental Materials 32 (2016) 54-64). (Year: 2016).*

* cited by examiner

METHOD FOR MANUFACTURING BONE GRAFT MATERIAL AND BONE GRAFT MATERIAL MANUFACTURED THEREBY

CROSS-REFERENCE TO RELATED APPLICATION

This application claims priority to and the benefit of Korean Patent Application No. 10-2018-0004840, filed on 15 Jan. 2018, the disclosure of which is incorporated herein by reference in its entirety.

BACKGROUND

1. Field of the Invention

The present invention relates to a method for manufacturing a bone graft material by using a 3D layered prototyping method (3D printing), and a bone graft material manufactured by using the method.

2. Discussion of Related Art

It is common that the existing implant surgery uses diagnostic equipment to primarily confirm clinical information on the oral cavity of a patient and is performed with a final confirmation at the time of actual surgery. In this case, various variables may be generated during the surgery, and when the response to the variables goes wrong, it is difficult to expect a clinically good prognosis, and inconvenience may be caused to the patient. Further, bone augmentation using a bone graft material in the form of a powder is performed on a patient who has difficulty in being subjected to implant surgery due to his or her lack of bone tissue. Also, in the case of a particle-type (powder-type) bone graft material, it is difficult to obtain a sufficient bone volume after the surgery. In order to solve the problem, a method of protecting a surgical site by introducing an excessive amount of bone graft material and using a shielding membrane is used, but there are disadvantages in that the surgical process is difficult to perform and the consumption of starting material is increased.

In order to solve this problem, there has recently emerged a method of manufacturing a bone graft material in a form which can be directly applied to a necessary site through a combination of digital clinical information and a 3D printer and operating on a patient. The method can solve a disadvantage in that a shielding membrane is necessarily used when an existing particle-type bone graft material is used, and can exhibit good performance even in maintaining bone volume. For this purpose, it is essential to develop a material capable of forming a 3-dimensional structure after a bone graft material is manufactured by synthesizing a raw material for a bone graft material suitable for 3D printing.

Currently, since bioceramics are the most chemically similar to the bone of a human body in being used as a synthetic bone graft material, it is known that bioceramics are a suitable material. However, 3D printing studies related to ceramic materials are more difficult than polymeric materials, so that many studies are not being conducted. However, it is possible to perform 3D printing with a material that can be implemented in vivo by processing a ceramic material into the form of a viscous paste and using a fused deposition modeling (FDM)-type 3D printer. This method is easy and can achieve a continuous output, but there are limitations such as deterioration in precision and restriction of design.

SUMMARY OF THE INVENTION

Thus, the present inventors conducted studies on a method for manufacturing a bone graft material using a 3D printing technology of a digital lighting processing (DLP) system in order to solve the aforementioned problems. That is, a slurry capable of being applied to 3D printing of a DLP system was developed by dispersing a ceramic material in a synthesized photocurable resin, and a bone graft material having a certain shape (for example, a block-type) was manufactured by utilizing the slurry. Consequently, when a bone graft material is manufactured by using a 3D printer of a DLP system, the bone graft material is stacked in a surface unit unlike an FDM system, so that bone graft material products having excellent precision can be manufactured. Further, the present inventors confirmed that the bone graft material of the present invention overcame the limitation of 3D printing of an existing FDM system by having an appropriate phase ratio, an excellent compressive strength, and the like, thereby completing the present invention.

Therefore, an object of the present invention is to provide a method for manufacturing a bone graft material using 3D printing of a DLP system, which is capable of improving a limitation such as deterioration in precision and restriction of design.

Another object of the present invention is to provide a bone graft material having a certain shape manufactured by the aforementioned method for manufacturing a bone graft material using 3D printing of a DLP system.

The present invention proposes a method for manufacturing a bone graft material in order to achieve the object and a bone graft material manufactured by the same.

The method for manufacturing a bone graft material of the present invention includes the steps of: (1) dispersing a powder material including calcium phosphate-based ceramics (hereinafter, referred to as 'a calcium phosphate-based ceramic material') in a solvent; (2) recovering the calcium phosphate-based ceramics by removing the solvent from a solution in which the calcium phosphate-based ceramic material is dispersed in Step 1; (3) producing a photocurable resin composition by adding a binder resin including a crosslinking agent and a photoinitiator to the calcium phosphate-based ceramics obtained in Step 2; (4) performing 3D rapid prototyping on a bone graft material molded body from the composition for a bone graft material produced in Step 3, that is, the photocurable resin composition, by 3D printing of a DLP system; and (5) debinding and sintering organic materials remaining in the bone graft material molded body subjected to prototyping in Step 4.

Here, the calcium phosphate-based ceramic material in Step 1 may include a single material or a mixture of two or more materials selected from monocalcium phosphate monohydrate, monocalcium phosphate anhydrous, calcium metaphosphate, dicalcium phosphate dihydrate, dicalcium phosphate anhydrous, calcium pyrophosphate, octacalcium phosphate, α-tricalcium phosphate, β-tricalcium phosphate, calcium-deficient hydroxyapatite, hydroxyapatite, tetracalcium phosphate, and amorphous calcium phosphate.

Here, as the calcium phosphate-based ceramic material, it is possible to use a mixture of hydroxyapatite and β-tricalcium phosphate in a ratio of 60:40 during the sintering in Step 5.

Further, the solvent used in Step 1 may include a single material or a mixture of two or more materials selected from ethyl alcohol, isopropyl alcohol, and acetone.

In this case, it is preferred that the amount of solvent is 200 wt % to 700 wt % based on the weight of the ceramic material.

In addition, Step 1 may further include the step of adding a dispersant including a single material or a mixture of two or more materials selected from a Tween surfactant, a Triton surfactant, and an anionic surfactant including linear alkyl benzene sulfonate, sodium lauryl sulfate, and sodium dodecyl sulfate.

In this case, it is preferred that a proportion of the added dispersant is 1 wt % to 10 wt % based on 100 wt % of the ceramic material.

Furthermore, the crosslinking agent used in Step 3 may include a single material or a mixture of two or more materials selected from acrylate-based and methacrylate-based resins including butyl acrylate, tert-butyl acrylate, 2-(diethylamino)ethyl acrylate, di(ethylene glycol) ethyl ether acrylate, ethylene glycol methyl ether acrylate, hexyl acrylate, 4-hydroxybutyl acrylate, 2-hydroxyethyl acrylate, isobutyl acrylate, isooctyl acrylate, methyl acrylate, 2-tetrahydropyranyl acrylate, 3-(trimethoxysilyl)propyl acrylate, allyl methacrylate, benzyl methacrylate, butyl methacrylate, tert-butyl methacrylate, cyclohexyl methacrylate, di(ethylene glycol)methyl ether methacrylate, 2-ethoxyethyl methacrylate, ethylene gylcol dicyclopentenyl ether methacrylate, ethylene glycol phenyl ether methacrylate, ethyl methacrylate, 2-hydroxyethyl methacrylate, isobornyl methacrylate, isobutyl methacrylate, isodecyl methacrylate, methyl methacrylate, phenyl methacrylate, propyl methacrylate, solketal methacrylate, tetrahydrofurfuryl methacrylate, 2-[(1',1',1'-trifluoro-2'(trifluoromethyl)-2'hydroxy)propyl]3-norbornyl methacrylate, and 3,3,5-trimethylcyclohexyl methacrylate.

Here, it is preferred that the crosslinking agent includes 2-hydroxyethyl methacrylate.

It is preferred that a proportion of the added acrylic and methacrylate resin crosslinking agent is 10 wt % to 40 wt % based on 100 wt % of the ceramic material.

Further, the crosslinking agent used in Step 3 may include a single material or a mixture of two or more materials selected from polyfunctional acrylic resins including glycerol propoxylate (1PO/OH) triacrylate, pentaerythritol tetraacrylate, pentaerythritol triacrylate, 1,3,5-triacryloylhexahydro-1,3,5-triazine, trimethylolpropane ethoxylate (1EO/OH) methyl ether diacrylate, trimethylolpropane propoxylate triacrylate, trimethylolpropane triacrylate, and tris[2-(acryloyloxy)ethyl] isocyanurate.

Here, it is preferred that the crosslinking agent includes tris[2-(acryloyloxy)ethyl] isocyanurate.

It is preferred that a proportion of the added polyfunctional acrylic resin crosslinking agent is 30 wt % to 65 wt % based on the ceramic material.

In addition, the photoinitiator in Step 3 may include a single material or a mixture of two or more materials selected from diphenyl(2,4,6-trimethylbenzoyl)phosphine oxide/2-hydroxy-2-methylpropiophenone, (benzene)tricarbonylchromium, 4,4'-bis(diethylamino)benzophenone, phenanthrenequinone, bis(2,4,6-trimethylbenzoyl)-phenyl-phosphineoxide, 2,4,6-trimethylbenzoyl-diphenyl-phosphineoxide, 2-benzyl-2-dimethylamino-1-(4-morpholinophenyl)-butanone-1, bis(eta5-2,4-cyclopentadien-1-yl)-bis(2,5-difluoro-3-(1H-pyrrol-1-yl)-phenyl)titanium, and diphenyl (2,4,6-trimethylbenzoyl)phosphine oxide.

It is preferred that a proportion of the added photoinitiator is 0.5 wt % to 10 wt % based on 100 wt % of the ceramic material.

Furthermore, Step 4 may further include irradiating the photocurable resin composition using a light source having a light wavelength of 280 nm to 460 nm (preferably 405 nm).

Moreover, a step of washing the bone graft material molded body subjected to prototyping may be included between Step 4 and Step 5.

Further, the sintering of the bone graft molded body in Step 5 may include the steps of increasing the temperature to 600° C. at a rate of 0.1° C. to 5° C. per minute, maintaining the temperature for 1 hour to 3 hours, increasing the temperature to 1,150° C. or 1,200° C. at a rate of 0.5° C. to 10° C. per minute, maintaining the temperature for 5 hours, and cooling.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Figure 1:
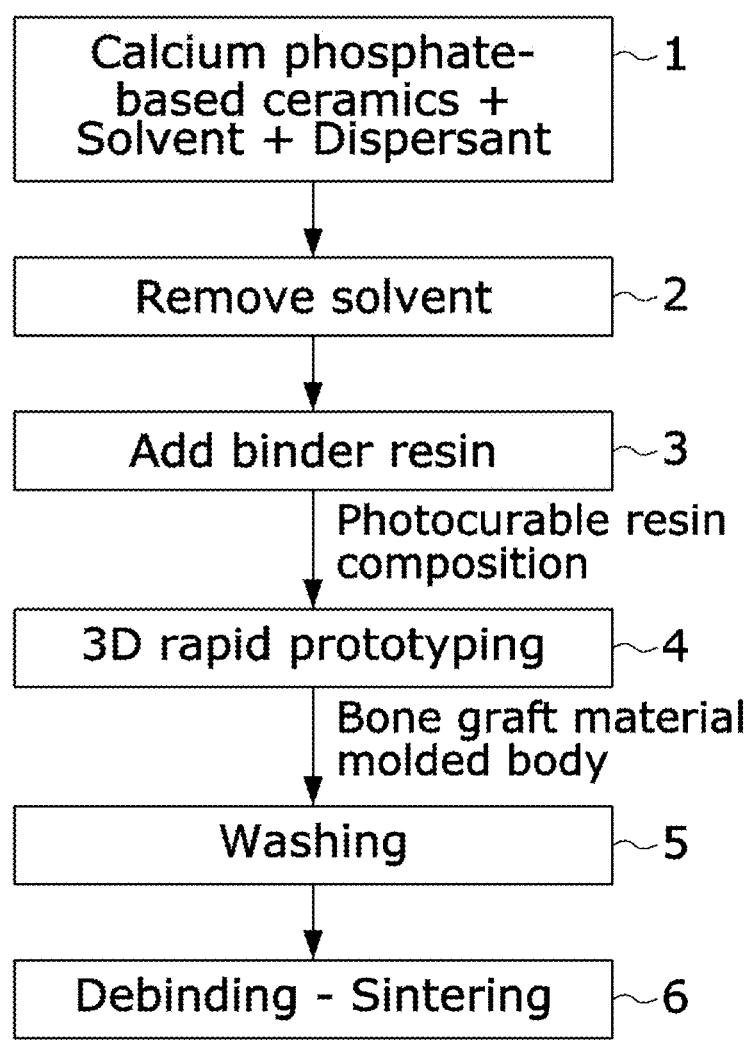
FIG. 1 is a process flowchart of a method for manufacturing a bone graft material of the present invention.

FIG. 1 is a process flowchart of a method for manufacturing a bone graft material of the present invention. The process is performed as follows.

[Step 1] dispersing a powder material including calcium phosphate-based ceramics including calcium and phosphorus (hereinafter, referred to as "a calcium phosphate-based ceramic material') including calcium and phosphorus into a solvent by using a dispersant;

[Step 2] recovering the calcium phosphate-based ceramics by removing the solvent from a solution in which the calcium phosphate-based ceramic material is dispersed in Step 1;

[Step 3] producing a photocurable resin composition which undergoes a curing reaction within a wavelength range of 280 nm to 460 nm (preferably 405 nm) by adding a binder resin, such as a crosslinking agent, and a photoinitiator to the calcium phosphate-based ceramics obtained in Step 2;

[Step 4] performing 3D rapid prototyping on a bone graft material molded body from the composition for a graft material produced in Step 3, that is, the photocurable resin composition by 3D printing of a DLP system;

[Step 5] washing the bone graft material molded body subjected to prototyping in Step 4; and

[Step 6] debinding and sintering organic materials remaining in the washed bone graft material molded body in Step 5.

Hereinafter, each step will be described in detail.

As the calcium phosphate-based ceramic material in Step 1, it is possible to use a single material or a mixture of two or more materials selected according to the ratio of calcium and phosphorus from monocalcium phosphate monohydrate, monocalcium phosphate anhydrous, calcium metaphosphate, dicalcium phosphate dihydrate, dicalcium phosphate anhydrous, calcium pyrophosphate, octacalcium phosphate, α-tricalcium phosphate, β-tricalcium phosphate, calcium-deficient hydroxyapatite, hydroxyapatite, tetracalcium phosphate, and amorphous calcium phosphate. Among these materials, it is preferable that during the sintering which is a final step of the steps of the method for manufacturing a bone graft material in FIG. 2, hydroxyapatite and β-tricalcium phosphate may be used in a mixture so as to have a ratio of 60:40.

For the solvent used in Step 1, ethyl alcohol, isopropyl alcohol, acetone, or a mixture thereof may be used, but the solvent is not limited thereto. Moreover, the amount of solvent may be included at 200 wt % to 700 wt % based on the weight of the ceramic material (a single material or a mixture thereof). When the amount of solvent is less than 200 wt %, the viscosity is so high that particles are not dispersed and mixed well; when the amount of solvent is more than 700 wt %, deterioration in efficiency in a ball mill process is caused.

For the dispersant used in Step 1, it is possible to use a Tween surfactant, a Triton surfactant, and an anionic surfactant such as linear alkyl benzene sulfonate, sodium lauryl sulfate, and sodium dodecyl sulfate, and it is also possible to use a mixture thereof. Moreover, as the proportion of the added dispersant, the dispersant may be added in an amount of 1 wt % to 10 wt % based on 100 wt % of the ceramic material (a single material or a mixture thereof). When the addition amount is less than 1 wt %, the dispersibility of ceramic particles deteriorates, so that a phenomenon in which particles settle down may occur during the 3D printing, which causes structural stability to deteriorate. When the addition amount is more than 10 wt %, this is not preferred because shrinkage may excessively proceed during sintering.

In the process of dispersing particles in Step 1, a heating reaction may be used, the temperature thereof may be more than 40° C. and less than 80° C. The heating method is not limited. When the temperature is less than 40° C., an accelerated reaction may be slowed down, and when the temperature is more than 80° C., the temperature causes the solvent to volatize.

Further, a reaction using microwaves may be used in order to accelerate the process of dispersing particles in Step 1. The reaction time may be more than 30 seconds and less than 5 minutes per one time. When the reaction time is less than 30 seconds, the accelerated reaction is not sufficiently performed, so that efficiency may be decreased; and when the reaction time is more than 5 minutes, an over-reaction of the composition may be caused.

In Step 2, it is possible to use a centrifuge, a heated stirrer evaporator, a rotary vacuum evaporator, and the like in order to remove the solvent from the slurry obtained in Step 1, and the method thereof is not limited.

For the crosslinking agent in Step 3, acrylate-based and methacrylate-based resins or a polyfunctional acrylic resin may be used:

First, for the acrylate-based and the methacrylate-based resins, it is possible to use butyl acrylate, tert-butyl acrylate, 2-(diethylamino)ethyl acrylate, di(ethylene glycol) ethyl ether acrylate, ethylene glycol methyl ether acrylate, hexyl acrylate, 4-hydroxybutyl acrylate, 2-hydroxyethyl acrylate, isobutyl acrylate, isooctyl acrylate, methyl acrylate, 2-tetrahydropyranyl acrylate, 3-(trimethoxysilyl)propyl acrylate, allyl methacrylate, benzyl methacrylate, butyl methacrylate, tert-butyl methacrylate, cyclohexyl methacrylate, di(ethylene glycol)methyl ether methacrylate, 2-ethoxyethyl methacrylate, ethylene gylcol dicyclopentenyl ether methacrylate, ethylene glycol phenyl ether methacrylate, ethyl methacrylate, 2-hydroxyethyl methacrylate, isobornyl methacrylate, isobutyl methacrylate, isodecyl methacrylate, methyl methacrylate, phenyl methacrylate, propyl methacrylate, solketal methacrylate, tetrahydrofurfuryl methacrylate, 2-[(1',1',1'-trifluoro-2'(trifluoromethyl)-2'hydroxy)propyl]3-norbornyl methacrylate, or 3,3,5-trimethylcyclohexyl methacrylate, or a mixture thereof. Preferably, 2-hydroxyethyl methacrylate may be used.

As the proportion of the acrylic and methacrylate resins which are a crosslinking agent, the resins may be added in an amount of 10 wt % to 40 wt % based on 100 wt % of the ceramic material (a single material or a mixture thereof). When the amount of the crosslinking agent is less than 10 wt %, the crosslinking reaction is so weak that the structural stability becomes weak; and when the amount of the crosslinking agent is more than 40 wt %, the shaped article may be easily broken by an external impact.

Further, for the polyfunctional acrylic resin used as a material for another crosslinking agent, it is possible to use glycerol propoxylate (1PO/OH) triacrylate, pentaerythritol tetraacrylate, pentaerythritol triacrylate, 1,3,5-triacryloylhexahydro-1,3,5-triazine, trimethylolpropane ethoxylate (1EO/OH) methyl ether diacrylate, trimethylolpropane propoxylate triacrylate, trimethylolpropane triacrylate, or tris[2-(acryloyloxy)ethyl] isocyanurate, or a mixture thereof. Preferably, tris[2-(acryloyloxy)ethyl] isocyanurate may be used. Moreover, as the proportion of the added polyfunctional acrylic resin, the polyfunctional acrylic resin may be added in an amount of 30 wt % to 65 wt % based on the ceramic material (a single material or a mixture thereof). When the amount is less than 30 wt %, the deformability of the shaped article is increased; and when the amount is more than 65 wt %, the periphery of the shaped article may be cured, so that the amount is not preferred.

For the photoinitiator, it is possible to use diphenyl(2,4, 6-trimethylbenzoyl)phosphine oxide/2-hydroxy-2-methylpropiophenone, (benzene)tricarbonylchromium, 4,4'-bis(diethylamino)benzophenone, phenanthrenequinone, bis(2,4,6-trimethylbenzoyl)-phenylphosphineoxide, 2,4,6-trimethylbenzoyl-diphenyl-phosphineoxide, 2-benzyl-2-dimethylamino-1-(4-morpholinophenyl)-butanone-1, bis(eta5-2,4-cyclopentadien-1-yl)-bis(2,5-difluoro-3-(1H-pyrrol-1-yl)-phenyl)titanium, or diphenyl(2,4,6-trimethylbenzoyl)phosphine oxide, or a mixture thereof.

Moreover, as the proportion of the photoinitiator, the photoinitiator may be added in an amount of 0.5 wt % to 10 wt % based on 100 wt % of the ceramic material (a single material or a mixture thereof). When the content of the photoinitiator is less than 0.5 wt %, the photocuring reaction may be weak during the 3D printing; and when the content is more than 10 wt %, prototyping stability may deteriorate because the amount of remaining unreacted initiator is increased, so that the content is not preferred.

Step 3 is a process of producing a composition by utilizing particles obtained through Step 2, and may be carried out until a slurry in a uniformly mixed form is formed. In addition, in the production of the slurry, it is possible to use an alumina mortar, an agate mortar, a high-speed rotary mixer, a stirrer and the like, and the mixing method thereof is not limited.

Step 4 is a process of manufacturing a bone graft molded body by subjecting the binder resin composition to 3D rapid prototyping (3D printing of a DLP system). After the composition produced in Step 3 is put into a dish for prototyping, the composition is cured by applying light to the composition using a light source having a light wavelength of 280 nm to 460 nm (preferably 405 nm). The curing condition is not limited.

Various molded bodies may be manufactured by setting conditions for model prototyping associated with a bone graft material such as design modification, thickness, and a supporter using software in conjunction with 3D rapid prototyping equipment in Step 4.

In order to wash an uncured material of a molded body completely subjected to prototyping in Step 5, ethyl alcohol, isopropyl alcohol, acetone, or a mixture thereof may be used, but is not limited thereto. Furthermore, the Step 5 is an optional process, which is not a process necessarily carried out.

Step 6 is a step of debinding organic materials such as a binder resin and a dispersant used in order to produce the photocurable resin composition in the previous Steps 1 and 3, and of sintering the organic materials in order to induce the growth of particles and improve strength.

The debinding is a process for removing organic materials such as the binder resin and the dispersant used in Step 3. It is preferred that a heat treatment is performed at 200° C. to 600° C. At a temperature less than that range, the organic materials may remain without being removed.

For the sintering, a heat treatment process is carried out at 1,100° C. to 1,200° C. In the case of a bone graft material, it is known that hydroxyapatite and β-tricalcium phosphate preferably have a ratio of (70 to 60):(30 to 40). When the temperature is less than 1,100° C., there is a problem in that strength is decreased; and when the temperature is more than 1,200° C., α-tricalcium phosphate may be produced.

Hereinafter, the present invention will be described in detail with reference to Examples to help understanding of the present invention. The following Examples are only for exemplifying the present invention, and the scope of the present invention is not limited to the following Examples. The Examples of the present invention are provided for more completely explaining the present invention to a person with ordinary skill in the art.

<Step 1>: Dispersion of Calcium Phosphate Ceramic Particles

Figure 2:
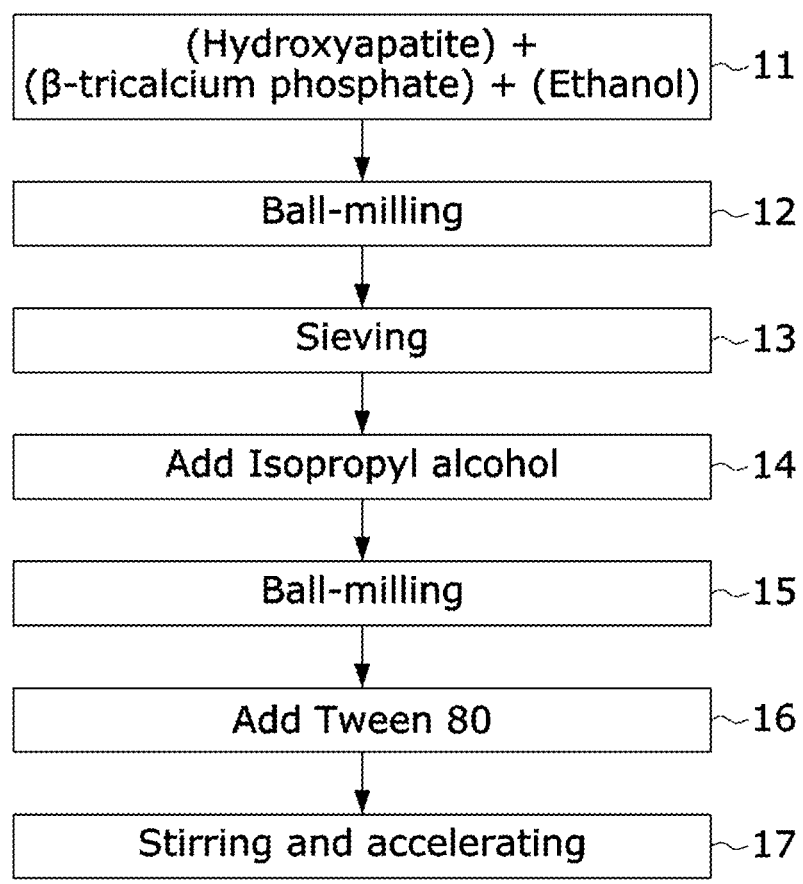
FIG. 2 is a process flowchart of the Implementation Example of Step 1.

FIG. 2 is a process flowchart of the Implementation Example of Step 1.

11: Ethanol was added to a mixture of hydroxyapatite and β-tricalcium phosphate as a starting material,
12: Ball-milling was performed, and then
13: A starting powder was produced by performing sieving.
14: 450 wt % of isopropyl alcohol based on the powder was added to 120 g of the powder,
15: Ball-milling was performed for 48 hours.
16: 3 wt % of Tween 80 based on the powder was added to the slurry produced in the previous 14 and 15, and then
17: An accelerated reaction was performed for 60 seconds by maintaining the temperature at 60° C., stirring the slurry at 500 rpm for 48 hours using a hotplate stirrer, and using microwaves once per 1 hour.

Figure 3:
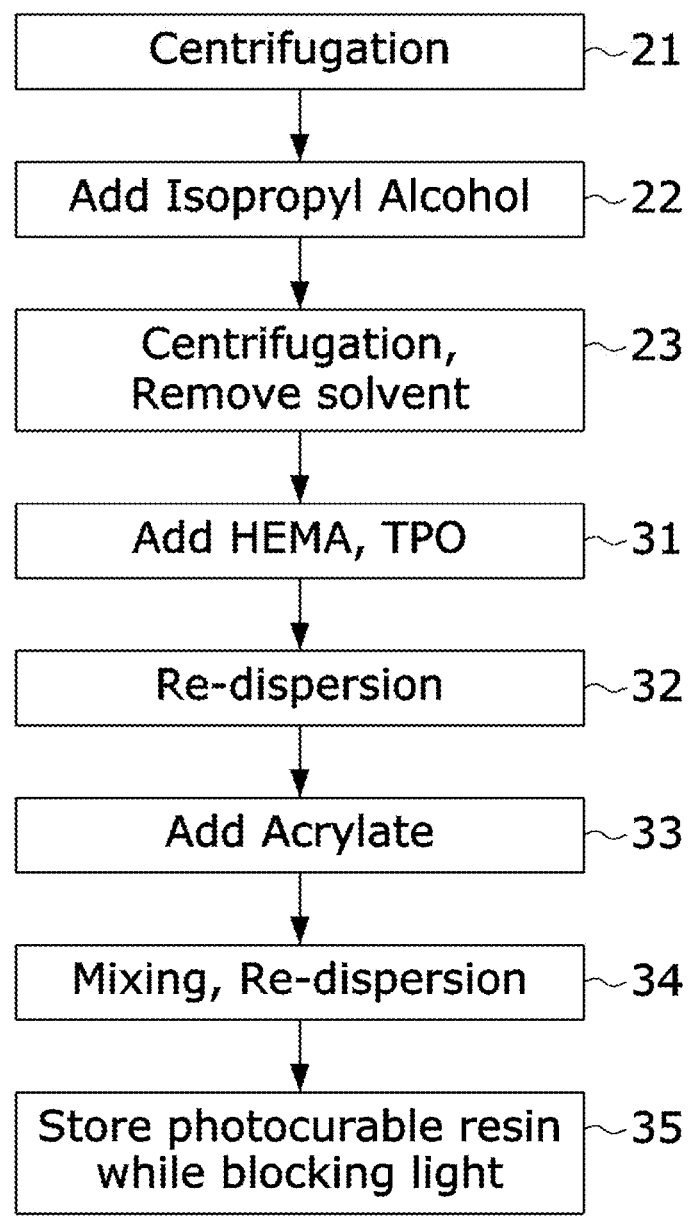
FIG. 3 is a process flowchart of the Implementation Examples of Steps 2 and 3.

<Steps 2 and 3> Removal of Solvent and Production of Photocurable Resin Composition FIG. 3 is a process flowchart of the Implementation Examples of Steps 2 and 3.

21: The calcium phosphate-based ceramic slurry prepared in Step 1 was put into a tube for centrifugation, and then unreacted particles and the solvent were removed by performing centrifugation at 5,000 rpm for 10 minutes using a centrifuge.
22: Isopropyl alcohol was again added thereto, and then
23: Centrifugation was performed at 7,000 rpm for 15 minutes by using a centrifuge, and then the solvent was removed.
31: 27 wt % of HEMA and 3 wt % of TPO based on 100 wt % of the ceramic material were sequentially added to the ceramic material, and then
32: Re-dispersion was performed with a vortex mixer in a state where light was blocked.
33: 30 wt % of an acrylate based on 100 wt % of the ceramic material was added thereto, and then
34: After mixing and re-dispersion were performed by using a vortex mixer, the composition was completely produced.
35: The photocurable resin composition completely produced was put into a container in which light was blocked and stored.

<Step 4>: 3D Rapid Prototyping

Figure 4:
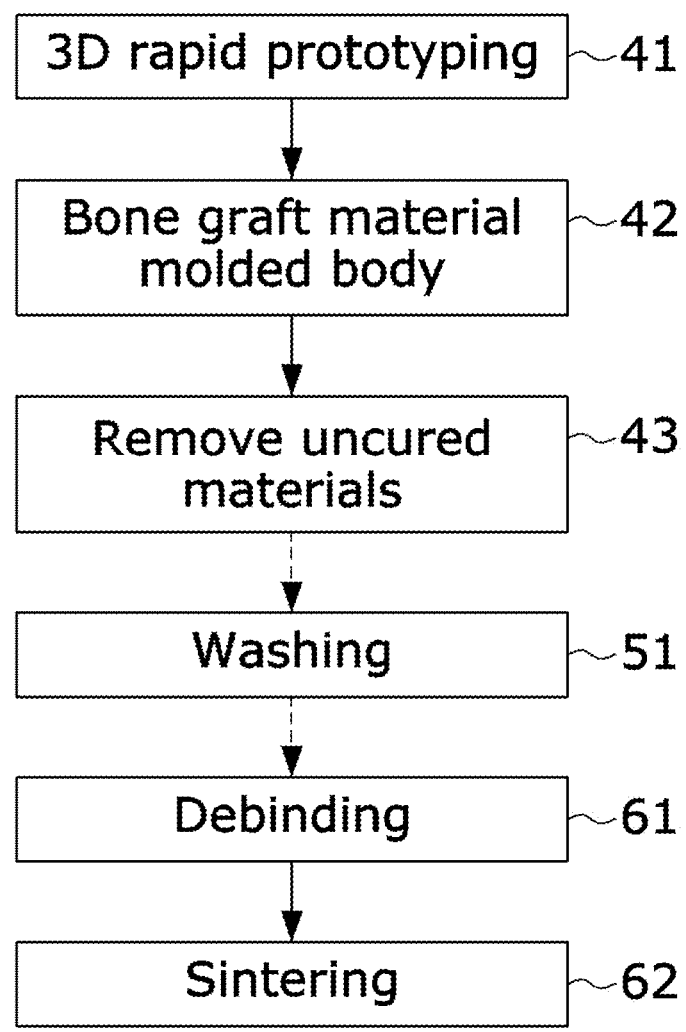
FIG. 4 is a process flowchart of the Implementation Examples of Steps 4, 5, and 6.

FIG. 4 is a process flowchart of the Implementation Examples of Steps 4, 5, and 6.

Figure 5:
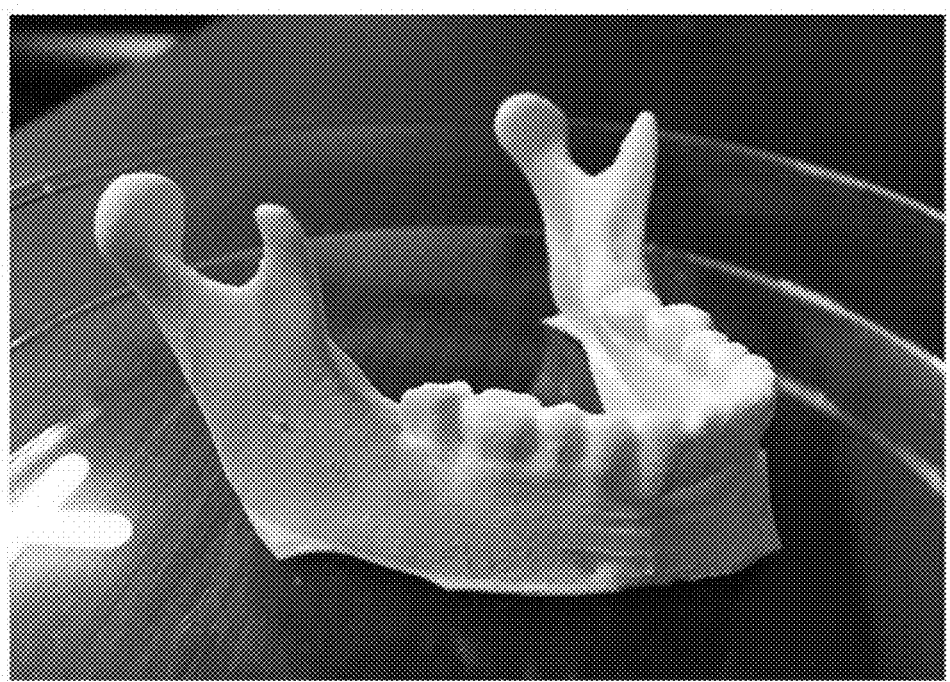
FIG. 5 is an exemplary photograph of a molded body obtained by performing prototyping on a bone graft material to obtain a form of a lower jaw model.

41: The produced photocurable resin composition was poured into a dish for 3D rapid prototyping, and then the dish was fastened to an equipment, and a bone graft material molded body was manufactured. 5 layers were subjected to prototyping after setting a prototyping thickness and an initial curing time to 30 μm and 20,000 ms, respectively, and then subjected to prototyping after setting the curing time to 4,000 ms.
42: The shape design when the bone graft material was subjected to prototyping was arbitrary. For example, it is possible to manufacture the bone graft material into a fully-packed cube shape (a cube with width, length, and height of approximately 10 mm, respectively). FIG. 5 is an exemplary photograph of a molded body obtained by performing prototyping on a bone graft material to obtain a form of a lower jaw model.
43: The completely manufactured molded body is stored after uncured materials are removed by using isopropyl alcohol.

<Steps 5 and 6>: Washing, Debinding, and Sintering of Manufactured Bone Graft Material Refer to FIG. 4 again.

51: A molded body, from which the uncured materials were removed, was washed. As previously mentioned, this washing step may be optionally performed.
61: In order to debind the bone graft material molded body molded in Steps 42 and 43, the bone graft material molded body was maintained at 200° C. for 2 hours after increasing the temperature to 200° C. at a rate of 0.2° C. per minute.

62: Thereafter, for the sintering treatment, the temperature was increased to 300° C. at a rate of 1° C. per minute, and the temperature was further increased to 500° C. at a rate of 0.2° C. per minute. After the temperature was maintained at 500° C. for 2 hours, the temperature was increased to 1,150° C. at a rate of 1° C. per minute, and then the temperature was maintained for 5 hours and cooled, thereby completing a final bone graft material.

<Analysis and Measurement>

X-Ray Diffraction Analysis of Sintered Bone Graft Material

An X-ray diffraction analysis of the sintered bone graft material according to Step 62 was performed.

Figure 6:
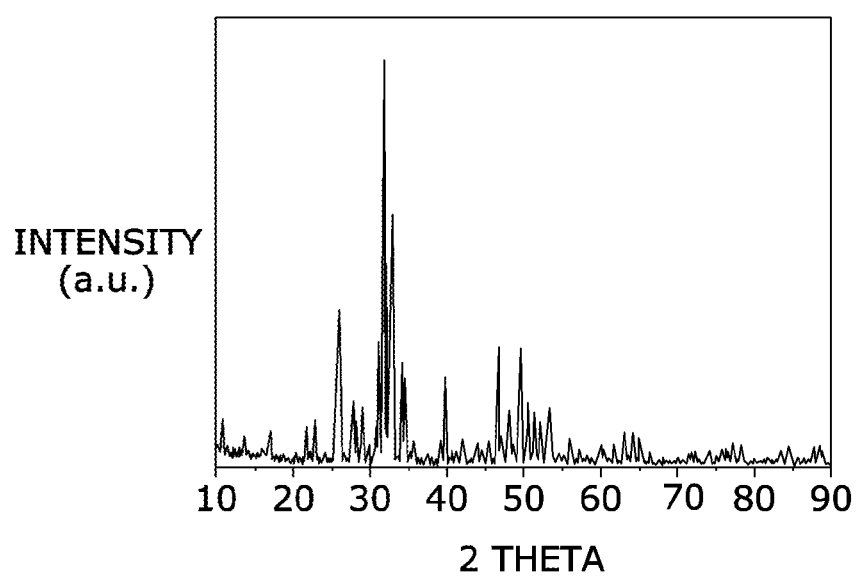
FIG. 6 is an X-ray diffraction analysis result.

FIG. 6 illustrates an X-ray diffraction analysis result. In this case, it was confirmed that the ratio of hydroxyapatite: β-tricalcium phosphate was (60 to 65):(40 to 35).

Measurement of Compressive Strength of Sintered Bone Graft Material

A compressive strength of the sintered bone graft material according to Step 62 was measured. It was confirmed that the average compressive strength was 6.84 MPa.

Observation of Microstructure of Sintered Bone Graft Material

A microstructure of the sintered bone graft material according to Step 6 was observed.

Figure 7A:
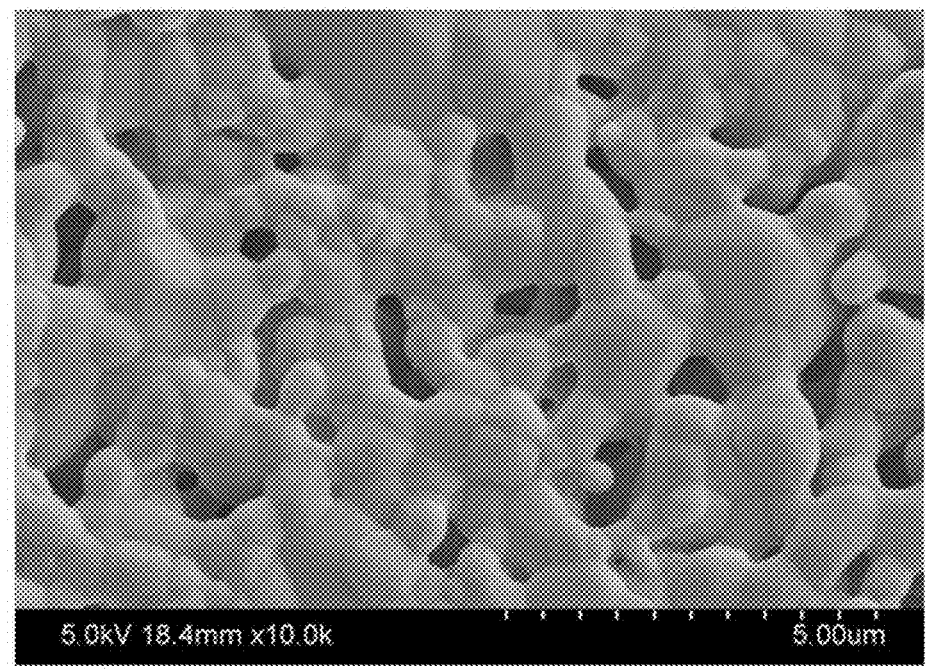
FIGS. 7A and 7B are SEM images showing a microstructure observed at different magnifications.
Figure 7B:
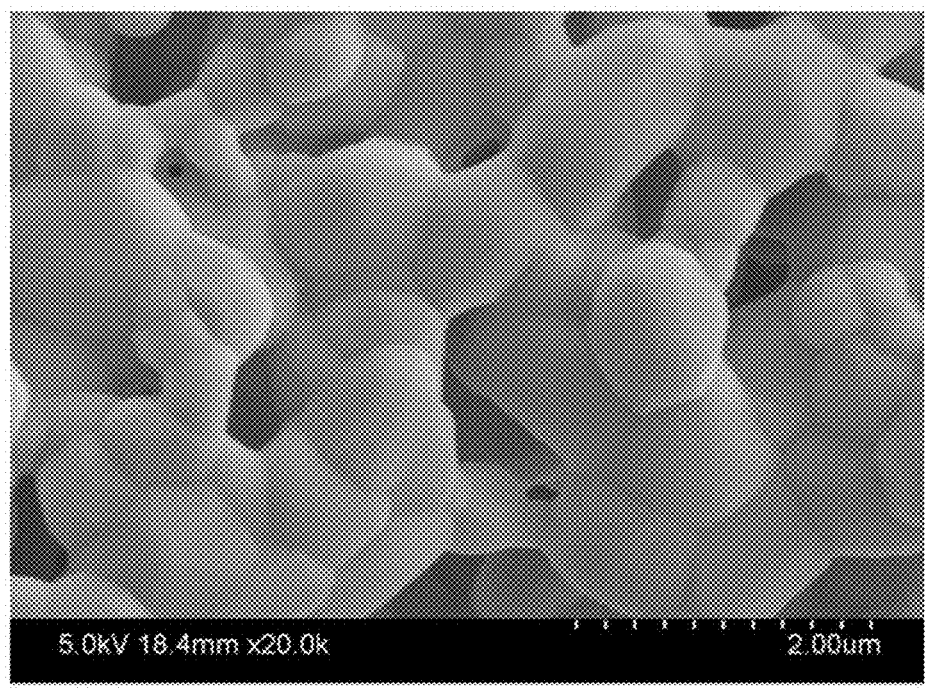

FIGS. 7A and 7B are SEM images showing a microstructure observed at different magnifications SBF Test of Sintered Bone Graft Material After the sintered bone graft material according to Step 6 was immersed in a simulated body fluid (SBF) solution, the sintered bone graft material was observed. It could be confirmed that an apatite layer was well formed.

Figure 8A:
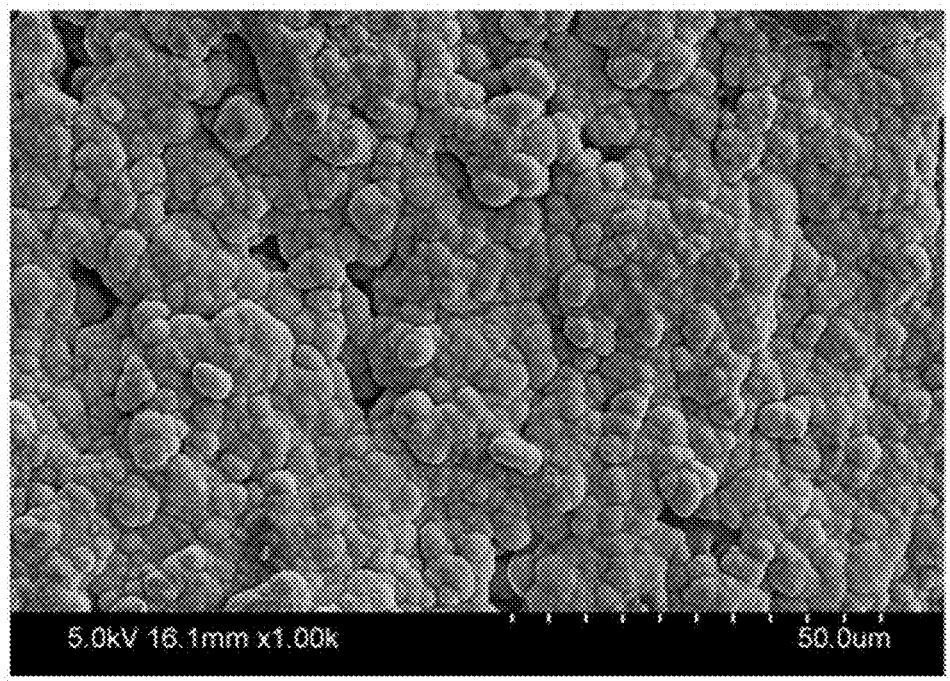
FIGS. 8A and 8B are SEM images showing a microstructure observed at different magnifications after the microstructure is immersed in an SBF solution for 24 hours.
Figure 8B:
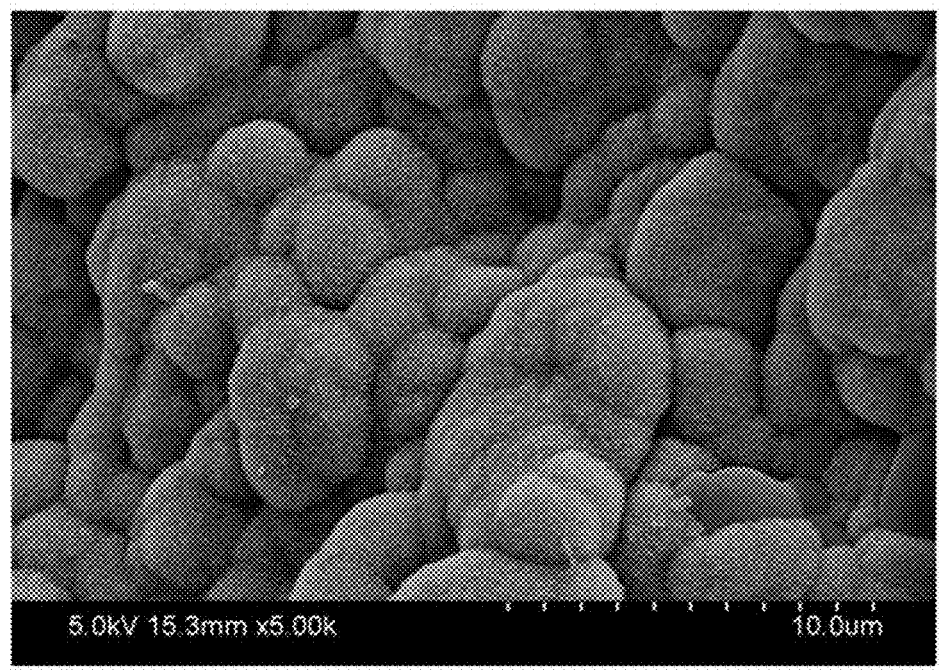

FIGS. 8A and 8B are SEM images showing a microstructure observed at different magnifications after the microstructure is immersed in an SBF solution for 24 hours.

According to the present invention, it is possible to overcome the limitation of 3D printing of an existing FDM system, for example, 3D rapid prototyping can be performed in order to obtain a sufficient bone volume even in the case of a patient who lacks bone tissue, a shielding membrane is not necessary when an existing particle-type bone graft material is used, and it is possible to use a 3D printer of a DLP system in which precision and designability are improved, so that a bone graft material product having excellent precision can be manufactured, and the bone graft material product has an appropriate phase ratio, an excellent compressive strength, and the like.

Since specific examples of the present invention have been described in detail above, the description includes only exemplary embodiments for a person with ordinary skill in the art, and the scope of the present invention is not limited thereby. Accordingly, the substantial scope of the present invention will be determined by the appended claims and their equivalents.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method for manufacturing a bone graft material, the method comprising the steps of:

(Step 1) dispersing a powder material comprising calcium phosphate-based ceramics in a solvent;

(Step 2) recovering the calcium phosphate-based ceramics by removing the solvent from a solution in which the calcium phosphate-based ceramics are dispersed in Step 1;

(Step 3) producing a photocurable resin composition by adding a binder resin comprising a crosslinking agent and a photoinitiator to the calcium phosphate-based ceramics obtained in Step 2;

(Step 4) performing 3D rapid prototyping on a bone graft material molded body from the composition for a bone graft material produced in Step 3, that is, the photocurable resin composition, by 3D printing of a DLP system; and (Step 5) debinding and sintering organic materials remaining in the bone graft material molded body subjected to prototyping in Step 4, wherein debinding includes removing the binder resin and the photoinitiator.

2. The method of claim 1, wherein the calcium phosphate-based ceramics in Step 1 comprises:

a single material or a mixture of two or more materials selected from monocalcium phosphate monohydrate, monocalcium phosphate anhydrous, calcium metaphosphate, dicalcium phosphate dihydrate, dicalcium phosphate anhydrous, calcium pyrophosphate, octacalcium phosphate, α-tricalcium phosphate, β-tricalcium phosphate, calcium-deficient hydroxyapatite, hydroxyapatite, tetracalcium phosphate, and amorphous calcium phosphate.

3. The method of claim 2, wherein the calcium phosphate-based ceramics in Step 1 comprises a mixture of hydroxyapatite and β-tricalcium phosphate in a ratio of 60:40 during the sintering in Step 5.

4. The method of claim 1, wherein the solvent used in Step 1 comprises a single material or a mixture of two or more materials selected from ethyl alcohol, isopropyl alcohol, and acetone.

5. The method of claim 1, wherein an amount of solvent is 200 wt % to 700 wt % based on a weight of the ceramic material.

6. The method of claim 1, wherein Step 1 further comprises a step of adding a dispersant comprising a single material or a mixture of two or more materials selected from a Tween surfactant, a Triton surfactant, and an anionic surfactant comprising linear alkyl benzene sulfonate, sodium lauryl sulfate, and sodium dodecyl sulfate.

7. The method of claim 6, wherein a proportion of the added dispersant is 1 wt % to 10 wt % based on 100 wt % of the ceramic material.

8. The method of claim 1, wherein the crosslinking agent used in Step 3 comprises:

a single material or a mixture of two or more materials selected from acrylate-based and methacrylate-based resins comprising butyl acrylate, tert-butyl acrylate, 2-(diethylamino)ethyl acrylate, di(ethylene glycol) ethyl ether acrylate, ethylene glycol methyl ether acrylate, hexyl acrylate, 4-hydroxybutyl acrylate, 2-hydroxyethyl acrylate, isobutyl acrylate, isooctyl acrylate, methyl acrylate, 2-tetrahydropyranyl acrylate, 3-(trimethoxysilyl)propyl acrylate, allyl methacrylate, benzyl methacrylate, butyl methacrylate, tert-butyl methacrylate, cyclohexyl methacrylate, di(ethylene glycol)methyl ether methacrylate, 2-ethoxyethyl methacrylate, ethylene gylcol dicyclopentenyl ether methacrylate, ethylene glycol phenyl ether methacrylate, ethyl methacrylate, 2-hydroxyethyl methacrylate, isobornyl methacrylate, isobutyl methacrylate, isodecyl methacrylate, methyl methacrylate, phenyl methacrylate, propyl methacrylate, solketal methacrylate, tetrahydrofurfuryl methacrylate, 2-[(1',1',1'-trifluoro-2'(trifluoromethyl)-2'hydroxy)propyl]3-norbornyl methacrylate, and 3,3,5-trimethylcyclohexyl methacrylate.

9. The method of claim 8, wherein the crosslinking agent used in Step 3 comprises 2-hydroxyethyl methacrylate.

10. The method of claim 8, wherein a proportion of the added acrylic and methacrylate resin crosslinking agent is 10 wt % to 40 wt % based on 100 wt % of the ceramic material.

11. The method of claim 1, wherein the crosslinking agent used in Step 3 comprises:
a single material or a mixture of two or more materials selected from polyfunctional acrylic resins comprising glycerol propoxylate (1PO/OH) triacrylate, pentaerythritol tetraacrylate, pentaerythritol triacrylate, 1,3,5-triacryloylhexahydro-1,3,5-triazine, trimethylolpropane ethoxylate (1EO/OH) methyl ether diacrylate, trimethylolpropane propoxylate triacrylate, trimethylolpropane triacrylate, and tris[2-(acryloyloxy)ethyl]isocyanurate.

12. The method of claim 11, wherein the crosslinking agent used in Step 3 comprises tris[2-(acryloyloxy)ethyl] isocyanurate.

13. The method of claim 11, wherein a proportion of the added polyfunctional acrylic resin crosslinking agent is 30 wt % to 65 wt % based on the ceramic material.

14. The method of claim 1, wherein the photoinitiator in Step 3 comprises:
a single material or a mixture of two or more materials selected from diphenyl(2,4,6-trimethylbenzoyl)phosphine oxide/2-hydroxy-2-methylpropiophenone, (benzene)tricarbonyl chromium, 4,4'-bis(diethylamino)benzophenone, phenanthrenequinone, bis(2,4,6-trimethylbenzoyl)-phenylphosphineoxide, 2,4,6-trimethylbenzoyl-diphenyl-phosphineoxide, 2-benzyl-2-dimethylamino-1-(4-morpholinophenyl)-butanone-1, bis(eta5-2,4-cyclopentadien-1-yl)-bis(2,5-difluoro-3-(1H-pyrrol-1-yl)-phenyl)titanium, and diphenyl(2,4, 6-trimethylbenzoyl)phosphine oxide.

15. The method of claim 1, wherein a proportion of the added photoinitiator used in Step 3 is 0.5 wt % to 10 wt % based on 100 wt % of the ceramic material.

16. The method of claim 1, wherein Step 4 further comprises a step of irradiating the photocurable resin composition using a light source having a light wavelength of 280 nm to 460 nm.

17. The method of claim 1, further comprising a step of washing the bone graft material molded body subjected to prototyping between Step 4 and Step 5.

18. The method of claim 1, wherein the sintering of the bone graft molded body in Step 5 comprises the step of increasing the temperature to 600° C. at a rate of 0.1° C. to 5° C. per minute, maintaining the temperature for 1 hour to 3 hours, increasing the temperature to 1,150° C. or 1,200° C. at a rate of 0.5° C. to 10° C. per minute, maintaining the temperature for 5 hours, and cooling.

19. A bone graft material manufactured by a method for manufacturing a bone graft material, the method comprising the steps of:
(Step 1) dispersing a powder material comprising calcium phosphate-based ceramics in a solvent;
(Step 2) recovering the calcium phosphate-based ceramics by removing the solvent from a solution in which the calcium phosphate-based ceramics are dispersed in Step 1;
(Step 3) producing a photocurable resin composition by adding a binder resin comprising a crosslinking agent and a photoinitiator to the calcium phosphate-based ceramics obtained in Step 2;
(Step 4) performing 3D rapid prototyping on a bone graft material molded body from the composition for a bone graft material produced in Step 3, that is, the photocurable resin composition, by 3D printing of a DLP system; and
(Step 5) debinding and sintering organic materials remaining in the bone graft material molded body subjected to prototyping in Step 4, wherein debinding includes removing the binder resin and the photoinitiator.

* * * * *